(12) United States Patent
Dang et al.

(10) Patent No.: US 11,717,418 B2
(45) Date of Patent: Aug. 8, 2023

(54) MEDICAL IMPLANTS AND OTHER ARTICLES OF MANUFACTURE BASED ON TRABECULAR BONE LATTICES

(71) Applicants: The Regents of the University of California, Oakland, CA (US); Alfred Li, Aurora, CO (US)

(72) Inventors: Alan Dang, San Francisco, CA (US); Alexis Dang, San Francisco, CA (US); Wenhan Chang, San Francisco, CA (US); Alfred Li, Aurora, CO (US)

(73) Assignees: The Regents of the University of California, Oakland, CA (US); Alfred Li, Aurora, CO (US)

( * ) Notice: Subject to any disclaimer, the term of this patent is extended or adjusted under 35 U.S.C. 154(b) by 198 days.

(21) Appl. No.: 17/040,453

(22) PCT Filed: Mar. 26, 2019

(86) PCT No.: PCT/US2019/024153
§ 371 (c)(1),
(2) Date: Sep. 22, 2020

(87) PCT Pub. No.: WO2019/191149
PCT Pub. Date: Oct. 3, 2019

(65) Prior Publication Data
US 2021/0022882 A1 Jan. 28, 2021

Related U.S. Application Data

(60) Provisional application No. 62/648,267, filed on Mar. 26, 2018.

(51) Int. Cl.
*A61F 2/44* (2006.01)
*A61F 2/30* (2006.01)

(52) U.S. Cl.
CPC ........... *A61F 2/447* (2013.01); *A61F 2/3094* (2013.01); *A61F 2002/3092* (2013.01);
(Continued)

(58) Field of Classification Search
CPC .......... A61F 2/44; A61F 2/442; A61F 2/4455; A61F 2/446; A61F 2/4465; A61F 2/447;
(Continued)

(56) References Cited

U.S. PATENT DOCUMENTS 7,208,222 B2 * 4/2007 Rolfe ...................... A61F 2/442
428/137
9,186,257 B2 * 11/2015 Geisler ................... A61F 2/447
(Continued)

FOREIGN PATENT DOCUMENTS

CN 103997991 A * 8/2014 ............. A61F 2/442
WO WO-2014059072 A1 * 4/2014 ............. A61F 2/442
(Continued)

*Primary Examiner* — Eric S Gibson
(74) *Attorney, Agent, or Firm* — Brian E. Davy; Bozicevic, Field & Francis LLP (57) ABSTRACT

Novel articles of manufacture based comprising lattices based on trabecular bone, having a plurality of plates and interconnecting rods. The trabecular bone-inspired lattice may be designed based on the general alignment of plates and rods found in trabecular bone, including anisotropic lattices having one or more predominant axes of mechanical strength. Lumbar fusion implants and other implants are provided having a trabecular bone inspired lattice in which bone graft material may be packed and providing a scaffold for bone fusion and growth. The implants may be based on bone structures having a predominant axis of mechanical strength and may be deployed in sites with the predominant axis of mechanical strength aligned with the primary axis of mechanical stress, such as in the the spine.

24 Claims, 8 Drawing Sheets (52) U.S. Cl.
CPC ............. *A61F 2002/3093* (2013.01); *A61F 2002/30593* (2013.01); *A61F 2002/30985* (2013.01); *A61F 2002/4495* (2013.01); *A61F 2310/00023* (2013.01); *A61F 2310/00029* (2013.01); *A61F 2310/00077* (2013.01); *A61F 2310/00161* (2013.01)

(58) Field of Classification Search
CPC .... A61F 2002/3092; A61F 2002/30985; A61F 2002/4495
See application file for complete search history.

(56) References Cited

U.S. PATENT DOCUMENTS

| | | | |
|---|---|---|---|
| 10,512,545 B2* | 12/2019 | Arnone | A61F 2/30767 |
| 10,772,732 B1* | 9/2020 | Miller | A61F 2/28 |
| 10,835,388 B2* | 11/2020 | Milz | A61F 2/447 |
| 11,065,126 B2* | 7/2021 | Newman | A61F 2/4611 |
| 11,160,668 B2* | 11/2021 | Nyahay | A61F 2/447 |
| 11,179,247 B2* | 11/2021 | Jebsen | A61F 2/447 |
| 11,213,405 B2* | 1/2022 | Bishop | A61F 2/4455 |
| 2005/0112397 A1 | 5/2005 | Rolfe | |
| 2007/0225810 A1 | 9/2007 | Colleran et al. | |
| 2010/0152857 A1 | 6/2010 | Freeman et al. | |
| 2011/0014289 A1 | 1/2011 | Datta et al. | |
| 2014/0107785 A1* | 4/2014 | Geisler | A61F 2/442 623/17.16 |
| 2014/0107786 A1* | 4/2014 | Geisler | A61F 2/447 623/17.16 |
| 2014/0236299 A1* | 8/2014 | Roeder | A61F 2/28 521/85 |
| 2014/0277461 A1 | 9/2014 | Nebosky et al. | |
| 2017/0020685 A1* | 1/2017 | Geisler | A61F 2/30965 |
| 2017/0224497 A1* | 8/2017 | Martin | A61F 2/30767 |
| 2017/0258606 A1* | 9/2017 | Afzal | A61F 2/4465 |
| 2017/0333205 A1* | 11/2017 | Joly | A61F 2/30771 |
| 2018/0256336 A1* | 9/2018 | Mueller | A61F 2/2846 |
| 2018/0296363 A1* | 10/2018 | Berry | A61F 2/28 |
| 2019/0117410 A1* | 4/2019 | Parry | A61F 2/447 |
| 2019/0134276 A1* | 5/2019 | Spiller | A61L 27/56 |
| 2020/0046512 A1* | 2/2020 | Newman | A61F 2/4455 |
| 2020/0188130 A1* | 6/2020 | Jebsen | A61F 2/447 |
| 2020/0297505 A1* | 9/2020 | McLaughlin | A61F 2/4455 |
| 2021/0022882 A1* | 1/2021 | Dang | F41H 5/02 |
| 2021/0213174 A1* | 7/2021 | Spiller | A61F 2/46 |
| 2022/0117753 A1* | 4/2022 | Rucker | A61F 2/442 |

FOREIGN PATENT DOCUMENTS

| | | | | |
|---|---|---|---|---|
| WO | WO-2016018160 A1 * | 2/2016 | ......... | A61F 2/30767 |
| WO | 2017223297 A1 | 12/2017 | | |
| WO | WO-2019191149 A1 * | 10/2019 | ......... | A61F 2/3094 |

* cited by examiner

MEDICAL IMPLANTS AND OTHER ARTICLES OF MANUFACTURE BASED ON TRABECULAR BONE LATTICES

CROSS-REFERENCE TO RELATED APPLICATIONS

This application is a 35 USC § 371 National Stage application of PCT International Application Number PCT/US2019/024153, entitled "Medical Implants And Other Articles of Manufacture Based On Trabecular Bone Lattices," filed Mar. 26, 2019, which claims the benefit of priority to U.S. Provisional Application Ser. No. 62/648,267, entitled "Novel Implants for Bone Fusion," filed Mar. 26, 2018; the contents which are hereby incorporated by reference.

STATEMENT REGARDING FEDERALLY SPONSORED RESEARCH OR DEVELOPMENT

Not Applicable.

BACKGROUND OF THE INVENTION

In the industrial sectors, one of the most definitive benefits of additive manufacturing (e.g., 3D printing) is the ability to reduce weight while maintaining mechanical performance. These advantages can result in lower material costs, significant reductions in production time and for industries such as aerospace and automotive, increased design flexibility.

Many products and objects rely on a lattice architecture to provide mechanical structure and form to the object, wherein the lattice is largely air space, resulting in reduced weight and material costs. To date, most lattices are generated by periodic mathematical functions which provide generally isotropic geometries that result in equal weight reduction and strength changes in all directions.

However, current lattices generally do not allow weight reduction with direction-specific strength (i.e. anisotropy). Accordingly, there is a need in the art for novel anisotropic lattice designs that can be readily implemented with 3D printing or other manufacturing techniques.

Meanwhile, in the medical context, interbody fusion is a common procedure applied in the treatment of spinal disorders. Interbody fusion is a surgical process wherein an implant and/or bone graft material is placed between two vertebrae. If the procedure is successful, new bone tissue growing within and extending from the implant ultimately creates a continuous structure fusing the two vertebra. The implant provides alignment of the vertebrae and mechanical support and guidance for the formation of the new bone tissue. Exemplary spinal interbody implants known in the art include, for example, the COALESCE™ thoracumbular device (NuVasive, Inc, San Diego, Calif., USA), comprising porous PEEK, the LUNA 3D™ Interbody Implant (Benvenue Medical Inc., Santa Clara, Calif., USA), comprising a modular system that is introduced in sections to minimize the invasiveness of the procedure; and the the CAPSTONE™ and CLYDESDALE™ implants, comprising titanium coated PEEK (Medtroinc PLC, Dublin Ireland).

Similar procedures outside of the axial skeleton where an implant and/or bone graft material is placed between two bony structures include corrective osteotomies of the upper and lower limb, repair or reconstruction of bone anatomy that has been disrupted with bone loss through trauma, infection, or tumor.

Currently, many interbody implants are available, comprising metal, medical plastics, cadaveric bone, medical ceramics, and other materials, including hybrids. These implants take on a variety of forms, including lattice structures or other geometries. While these implants are often effective, significant room for improvement exists. A first problem with spinal interbody implants and other implants placed for the intent of bony fusion is subsidence. Subsidence is the implant device sinking or burrowing into one or both of the adjacent vertebra or bony structures between which the implant is sandwiched. Subsidence results in loss of mechanical structural support, which can result in movement or slippage of the implant, weakening the bone graft or causing its failure as well as alteration to the alignment of the structures intended to be fused.

Another issue in fusion processes is the failure or poor growth of the bone graft material. Successful fusion of the two vertebra requires biologic integration between the adjoining vertebral bones or other bony structures. This can be bone outgrowth of the implanted bone graft material or ingrowth into the bone graft and device. The environment provided by the implant makes a significant contribution to the development of new bone tissue. Interbody implants comprise one or more graft windows within which bone graft material is placed and develops. Current graft window designs range from hollow spaces to porous geometric lattices. Fusion failure is common for all such devices, and there is an ongoing need for improved graft environments that facilitate vigorous bone growth.

A third issue is the ergonomics and fit of the implant. In contrast to the use of bony spacers in osteotomy procedures where a surgeon has created flat surfaces for the placement of the implant, when placing an interbody device between two vertebrae, areas of poor fit are common due to the irregular topography of the site. The surgeon often must shave away bony material on one or both of the vertebrae in order to fit and properly place the implant. This extra intervention may result in inflammation and injury, as well as increasing the complexity and expense of the procedure. Excessive removal of the bony material may also weaken the mechanical strength of the vertebral bony surface, leading to an increased risk of subsidence. Accordingly, there remains a need in the art for improved implant architectures that minimize or reduce the need for surgical modification of the target vertebrae.

In a related aspect, there is a need in the art for improved customization. The inherently high level of heterogeneity among individuals in the shape of their vertebra means that no single implant design can effectively fit all patients. The primary loading direction may also be different depending on the patient's standing or seating alignment (sagittal balance) as well as the particular location of the fusion site and its relationship to the overall curvature of the spine. Accordingly, there is a need for improved interbody implant platforms that can be readily customized to the specific architecture of each fusion site.

SUMMARY OF THE INVENTION

The scope of the invention is directed to novel lattice structures based on trabecular bone. Such structures will be termed "trabecular bone-inspired lattices" or "TBI lattices. The TBI lattice design represents the novel adaptation of highly evolved natural structures, including trabecular bone. Trabecular, or cancellous bone, as found in native bone tissue, is a porous bone comprising a lattice of bony processes, called trabeculae. The trabeculae consist of a complex heterogeneous distribution of interconnecting rod-like and ribbon or plate-like structures. These rods and plates are largely aligned to provide mechanical strength along the primary axis of stress in the bone while also providing sufficient biomechanical strength against other vectors of stress as well as porosity or open channels allowing the transit of cells, fluids, and other materials through the structure and within the structure.

In a first aspect, the inventors of the present disclosure have advantageously determined that a trabecular bone structures may be mimicked in the construction of manufactured items, wherein superior strength to weigh ratios and anisotropic strength profiles may be imparted.

In a second aspect, provided herein are novel interbody devices, and other implant devices, embodying various improvements to the art. The novel inventions disclosed herein provide the art with improved devices and methods of achieving bone fusion for lumbar treatments, long bone corrective osteotomies, and other procedures.

DESCRIPTION OF THE DRAWINGS

FIG. 1A and FIG. 1B.

FIG. 2A and FIG. 2B.

FIG. 3A, FIG. 3B, FIG. 3C, and FIG. 3D.

FIGS. 4A, 4B and 4C.

FIGS. 5A, 5B, 5C, and 5D.

DETAILED DESCRIPTION OF THE INVENTION

The TBI lattice design represents the novel adaptation of highly evolved natural structures, including trabecular bone. Trabecular, or cancellous bone, as found in native bone tissue, is a porous bone comprising a lattice of bony processes, called trabeculae. The trabeculae consist of a complex heterogeneous distribution of interconnecting rod-like and ribbon or plate-like structures. These rods and plates are largely aligned to provide mechanical strength along the primary axis of stress in the bone while also providing sufficient biomechanical strength against other vectors of stress as well as porosity or open channels allowing the transit of cells, fluids, and other materials through the structure and within the structure.

The inventors of the present disclosure have advantageously determined that a trabecular bone structures may be mimicked in the construction of manufactured items, wherein superior strength to weight ratios and anisotropic strength profiles may be imparted.

In a primary embodiment, an object comprising at TBI lattice, wherein the TBI lattice comprises
   a plurality of plates, wherein each plate comprises a ribbon structure comprising a length, width and thickness and having a predominant axis; and
   a plurality of rods, wherein each rod comprises an elongated structure and wherein the plurality of rods interconnects the plates with one another.

A first element of the TBI lattice is the plate. The TBI lattice will comprise a plurality of plates, each of which is a ribbon-like body having a large length, a small width, and a small thickness. A typical plate will have a width that is between 2 and 50 times its thickness, for example a width to thickness ratio of at least 2, at least 3, at least 4, at least 5, at least 6, at least 8, at least 10, at least 15, at least 25 at least 30, at least 50 times the thickness. It will be understood that this ratio may comprise a constant ratio (plates all of the same width) or an average ratio for plates having variable width, such as an undulating width, a width that varies by irregular intervals, such as is found in actual trabecular bone, or a width that is larger in localized areas of the lattice requiring extra strength, such as at the end points of the plate where they meet each other or meet an external element such as a cage structure, as described below. For example, in one embodiment, the plate may be substantially an elongated rectangle. In another embodiment, the plate may comprise an irregular, elongated shape, for example with protrusions, indentations, holes, and other irregular features found in the organic forms of trabecular bone plates.

Meanwhile, the length of the plate will generally be several times the width of the plate, depending on the length of the object and the degree of coiling/twisting of the plate. For example, plates of 2 to 100 times the width of the plate may be used, for example a length to width ratio of at least 2, at least 3, at least 4, at least 5, at least 6, at least 8, at least 10, at least 15, at least 25 at least 30, at least 50 or at least 75 times the thickness.

Exemplary plate geometries are provided as examples. For example, a plate may have a length:width:thickness ratio of about 5:5:1, about 5:2:1, about 10:3:1, about 10:5:1, about 20:2:1, about 20:5:1, about 50:10:1, about 50:5:1, about 50:2:1, about 100:10:1, about 100:5:1, or about 100:2:1 50:10:1, about meaning within 5% or 10% of the enumerated value.

The plates may also have a ribbed or irregular concave or convex surfaces to increase surface area. The ratios from 1:1:1 to x:y:z generally covers all geometries, with more symmetric cross sections relative to the length reflecting rods while more asymmetric cross sections relative to the length reflecting plates. The specific parameters vary based upon the material used and intended structural design parameters.

In a TBI lattice, one or more sets of plates will be present. Each such set of plates will align along an axis of the lattice wherein enhanced load support is desired. In one embodiment, the TBI lattice will comprise a predominant axis of mechanical strength, being an axis along which the lattice has the greatest mechanical strength, i.e. for a selected measure of mechanical strength such as resistance to compression, hardness, resistance to bending, or other measure of mechanical strength known in the art. Each plate will have a predominant axis, comprising the general alignment of the plate, however, the plate will typically be undulating or twisted, i.e. deviating from the predominant axis in sections. The undulation contributes to anisotropic strength reducing stress at the junctions between plates and rods, contributes to increased surface area which is generally desired, and can contribute to improved ease of manufacturing. For example, the plates may be twisted, for example in a helical manner. The terminal end of each plate may attach to a cage element which encircles the lattice, or it may terminate by joining another plate, such that a branched structure is formed. Plates having different predominant axes may connect or may be independent of one another.

The TBI lattice will further comprise a plurality of rods. Each rod comprises an elongated structure, such as a tube, strut, or irregular protrusions. The network of rods provides interconnectivity to the lattice by connecting plates together. Rods may be straight or may have an irregular, undulating or twisting orientation. Each end of a rod will in a connection with a plate (or another rod, to form branching structures). Rods may also terminate by a connection to the surrounding cage elements. Rods may be flat, square, circular, or irregular.

Length:width:thickness ratios describing rods may be of any generally elongated form, for example, with geometries such as about 1:1:1 up to 10:1:1, for example, various geometries such as about 3:1:1, about 5:2:1, about 10:2:1 or about 10:1:1, with about being within 5% or 10% of the enumerated value. Fore example, a 3 mm length rod or rectangular beam with a 1×1 mm cross section all the way to a larger 30 mm length rod that may have a 1×1 mm cross section or even a 3×3 mm cross section. The ratios may vary throughout the length, reflecting a cone-like structure, for example, starting with an initial cross-section of 1×1 mm all the way to a larger cross section of 3×3 mm in areas requiring additional strength or in portions of connectivity. It should also be understood that the ratios may be expressed as approximate or gross estimates, an ellipsoid cross section with a ratio of 1:1.2 would still be understood have a "rod-like" structure.

In one embodiment, the TBI lattice is anisotropic, wherein the predominant axes of the individual plates align along one or more axes. In one embodiment the majority of plates align along a single axis, imparting strength along this predominant axis. For example, over 40%, over 50%, over 60% over 70%, over 80% or over 90% of the plates may align along a predominant axis. For example, "aligned" plates may include plates whose predominant axis diverge from one another by less than 1 degree, less than 5 degrees, less than 10 degrees, less than 15 degrees, or less than 20 degrees. In another embodiment, the subsets of plates align along two or more divergent axes, imparting strength along multiple axes.

The TBI lattice may further comprise a cage structure, being any wall, cage, or other structure forming an outer shell or lattice, which may comprise the form of the object to be filled by the TBI lattice. For example, the cage may comprise a plurality of ribs that define the outer form of the lattice and which serve as connection points for the elements of the TBI lattice. Cage ribs may be connected in a regular or irregular pattern (e.g. a substantially square mesh). In an alternative implementation, the lattice is self supporting and the terminal ends of the plates are not connected to shared structures. Cavity closing materials, such as thermoset resins, may be used to enclose the lattice and provide an outer surface around the lattice. A cage may also be manufactured in the same material as the lattice and closing, such as a tube or pipe with an internal lattice structure.

In some embodiments, the TBI lattice is not encased in any outer structure, wherein the form of the object is defined by the endpoints of the plates and rods.

The configuration of the plates and rods may be tuned to create a lattice with the desired properties. For example, the properties may be tuned to attain a desired measure of mechanical strength, including, for example, resistance to torsion, resistance to compression, or resistance to bending, yield strength, tensile strength, fatigue strength, crack resistance. Optimization of the variables for a desired application may be made using engineering software packages known in the art. For example, for increased resistance to torsion, the connectivity density should be higher. For increased resistance to compression, the orientation of the plates should be anisotropic in the orientation of the compression stress. For increased resistance to bending, plate and/or rod thickness may be increased.

The lattice may comprise localized regions of increased mechanical strength, imparted, for example, by one or more properties, such as increased numbers or density of plates, increased width and/or thickness of plates, increased density of rods (greater localized interconnectivity), increased width, thickness, and/or diameter of rods, increased alignment of plates. "increased" in this context means greater than in areas of less mechanical strength, for example greater than the bulk average value of the enumerated variable in the lattice as a whole. For example, if the bulk density of plates in a particular TBI lattice is 50% by volume, a localized area of increased plate density would be any region having a bulk plate density of greater than 50%. In areas of localized increased mechanical strength, variables that impart strength may be increased, for example, by greater than 10% increased, greater than 20% increased, greater than 30% increased, greater than 40% increased, greater than 50% increased, greater than 60% increased, greater than 70% increased, greater than 80% increased, greater than 90% increased, greater than 100% increased, greater than 200% increased, greater than 300% increased, greater than 500% increased, or greater than 1000% increased.

Variables that may be adjusted in a TBI lattice include:
Plate length, width, thickness;
Plate surface (smooth vs. ribbed vs. holey);
Plate density (how many plates per unit volume);
Predominant axes (one or more axes wherein a set of plates is aligned along each such axis);
Degree of anisotropy, which assess the degree to which elements are oriented along an axial direction (degree to which plates deviate from their predominant axis);
Number of predominant axes (one or more axes which have the greatest ability to resist compressive forces);
Rod shape;
Rod density;
Rod orientation;
Rod surface;
Connectivity density, measuring the degree of interconnectivity of individual elements of the lattice; and
Overall density (e.g. air space fraction) of the lattice
Additional quantitative measurements to describe lattice geometry include structural model index (SMI), and ellipsoid factor (EF). SMI uses the change in surface area as volume increases infinitesimally to provide a numerical description of the overall geometry where 0 represents pure plates, 3 for pure rods and 4 for pure solid spheres and is commonly used to describe this geometry. A limitation of SMI is that concave structures are assigned negative numbers.

The EF addresses the limitation of SMI and uses the axis lengths from prolate, oblate and intermediate ellipsoids to determine how prolate or oblate the trabecular space is at a particular point. Highly prolate (javelin-shaped, rod-like) ellipsoids have a single long axis (c) and two short axes (a, b) such that a<b<<c, whereas highly oblate (discus-shaped, plate-like) ellipsoids have two longer axes (b, c) and one much shorter axis (a) so that a<<b<c. Calculating EF as the difference in ratios, EF=a/b−b/c leads to a useful scale ranging from −1 (oblate, a/b~0; b/c~1) to +1 (prolate, a/b~1; b/c~0). EF of 0 indicates an intermediate ellipsoid where a/b=b/c, which is the case for spheres (a=b=c) and other ellipsoids with axis ratios a:qa:$q^2$a. A value of −1 represents a more discus shape and a value of 1 represents a more javelin shape. A mean value of 0.08 represents an intermediate state between plate and rod like geometry, with a slight shift to rod-dominated structures.

The SMI can range from 0.5 to 3.5 depending on the desired strength, flexibility, or porosity of the lattice. SMI values outside this range such as an SMI less than 0.5 may be used when maximum strength is needed and there is low concern for excessive pressure or stress on the surfaces or low need for interconnectivity.

The EF can range from −0.5 to 0.5 depending on the desired strength, flexibility, or porosity of the structure. EF values outside of this range such as an EF less than −0.5 may be used when maximum strength is needed and there is low concern for excessive pressure or stress on the surfaces or low need for interconnectivity.

The degree of anisotropy can range from 0.5 to 3.0 depending on the desired strength or porosity of the structure.

The total volume of lattice material relative to overall volume of lattice may have a range of 5 to 90%, for example 10-80%, 20-70%, 30-60% or 40-50%, including intermediate values of the enumerated ranges. Depending on the desired properties of the TBI lattice, the air spaces may be infiltrated with other materials, for example, resins, foam, or other materials that can be formed from liquid precursors and subsequently solidified, hydrogels, or dry powdered materials encased or enclosed by another material.

In one embodiment, the anisotropic lattice is self-supporting (not manufactured or deployed within or on any supporting members) and can be 3D printed without support structures. In several embodiments of the invention, the self-supporting structure is robust enough to have other regular lattices such as grids or single hollow structures spanning an axis of the interbody device. In one embodiment, if visibility across the graft window is desired, for example, for radiographic assessment of bone-through-growth or fusion, a window may be included wherein visualization by radiographic imaging is possible. Such visibility may be beneficial when the interbody device is manufactured with a radioopaque material such as Ti6Al4V-ELI.

Trabecular Bone Replica. In one implementation, the TBI lattice comprises a three-dimensional replica of actual trabecular bone. The trabecular bone mimic structure is created by first scanning a selected trabecular bone sample volume with a suitable imaging modality for three dimensional scanning, for example by CT or MR imaging, or tomographic histology. The scanned volume of bone is then recreated from the scan by a suitable fabrication means, for example, by a 3D printer, as known in the art, or similar additive fabrication process. For example, the replica trabecular bone lattice may comprise a reproduction of bone from a vertebrae or other bony structure in the body. Exemplary strong templates include lumbar spine trabecular bone, which generally has a balance of plates and rods. Femur bone is also very strong, generally having more plates than rods.

It will be understood that the trabecular bone replica may comprise a structure that is substantially identical to the scanned bone from which it is derived. In other implementations, the trabecular bone replica is modified from the bone from which it is derived, for example, being smoothed or simplified or being supplemented with additional structures. The trabecular bone structural mimic may replicate the original bone structure with any desired degree of resolution, for example at the 1 micron to 5 mm feature scale, as limited by the resolution of the scanning and fabrication systems. Advanced imaging systems, such as micro CT can scan the target bone at 1 micron volume (0.001 mm) resolution. Metal fabrication techniques such as e-beam or laser can produce lattices with very high resolution replicas, for example, e-beam can replicate features as small as 140 μm and laser can replicate features down to about 100 μm in size. PEEK printing, for example by FDM or laser melting, can create features in the range of 0.1 mm in size.

The trabecular bone TBI lattice may be recreated at any desired scale, for example as an actual size replica, or as a miniaturized or enlarged replica, e.g. in the range of 1-5,000% of the original bone size. The scale allows additional design flexibility when using a TBI lattice. A dense microscale TBI lattice with thin walls and sparse macroscale TBI lattice with thicker walls can be used to provide similar biomechanical strengths, however the denser TBI lattice may act as a better sieve or flow restrictor if fluid or other materials are to be passed through the TBI lattice. Different densities of the TBI lattice can also be used to alter the thermal properties of the lattice in terms of surface area for heat exchange or passive heat sinking/thermal conductivity.

In one embodiment, the bone on which the trabecular bone replica is based is a bone having a predominant axis of mechanical strength. Accordingly, the TBI lattice will have a predominant axis of mechanical strength, for example, an axis having an increased number or density of plates or thicker plates. In one implementation, trabecular bone are obtained from a bone wherein the bone is typically under a directional stress, for example spinal trabecular bone typically under a superior to inferior stress supporting the body, or a leg bone primarily under superior to inferior axis stress in supporting the body against gravity. Bone structures having a predominant axis of stress may be scanned, and a TBI replica or inspired lattice recreated by 3D printing or like additive manufacturing method. The TBI lattice may then be deployed in a setting having a predominant axis of stress, wherein the predominant axis of stress to which the lattice is subjected is substantially aligned with the predominant axis of stress of the bone from which the lattice is derived. For example, trabecular bone of the vertebrae or leg will have a predominant axis of stress, superior to inferior, to which the bone is subjected. Replica trabecular lattices based thereon may be deployed such that the inferior to superior axis of the source bone is aligned with the predominant axis of stress to which the lattice will be subjected or wherein maximum mechanical strength is desired.

Use of TBI lattice for mechanical strength. Traditional use of lattice structures, or latticing of solid structures have been to reduce the weight of a part, while maintaining strength. The baseline device is a solid part with assumed isotropic strength needs. For many applications, however, the need is not for an isotropic part. Optimization of the strength of a part, in the direction of its intended stresses, i.e. creation of an anisotropic part may yield a part that is superior in actual strength in its application while also being lighter. These anisotropic lattices allow for optimization of structure based upon intended application. Currently iterative design approaches are being utilized to optimize material structure, but this is still based upon having solid beams and struts. The next generation of design iteration will be able to optimize for internal structure (with latticing option), to further optimize the modulus, and therefore function of parts.

This anisotropic lattice can also be effective for shock absorption and cushioning applications. These are applications that are designed to resist compressive loads. Based upon the source of this bio-derived structure, this optimization against compressive loads has been optimized through Wolff's Law with the bone structure shaped by the loading forces Manufacturing and Materials. The TBI lattices of the invention may be produced by any suitable means in the art, including by molding, milling, weaving, or printing. The structures of the invention may comprise a single piece, or may comprise multiple components joined to form the lattice, for example by adhesives, welding, interlocking structures, or fastening structures. The lattices may comprise a single material or may comprise a mix of materials.

Generally, the complex three-dimensional structures of the invention will be made by additive manufacturing processes, as known in the art. additive manufacturing encompasses any number of manufacturing processes for the creation of complex three dimensional objects. Generally, objects models are produced by CAD or like software, wherein the object is made up of a series of layers. The objects are then created layer by layer in specialized devices. For example, powdered material may be injected to a substrate where an addressable energy source such as plasma, laser beam, or electron beam is directed to melt the powder and fuse it to the underlying substrate The TBI lattices may comprise any suitable material. For example, the lattice may comprise metal or polymeric material. Exemplary metals include stainless steel, titanium, aluminum, copper, cobalt chrome, and other alloys. Exemplary polymeric materials include polyether ether ketone (PEEK) or PEKK, ultrahigh molecular weight polyethelene, polyphenylsulfones, polyetheramide materials, polylactic acid, nylons, and other thermoplastics. Weaving with carbon fiber reinforced plastics another similar woven structures can also be used. Exemplary titanium materials include Ti6Al4V-ELI. In some embodiments, the lattice will comprise a combination of two or more materials. In one embodiment, the lattice is printed from a polymeric material such as PEEK and is subsequently coated (e.g. by dipping, spraying, or any other coating technology) with metal or other materials. Surface treatments may also be applied to the metals or plastics to alter the biomechanical strength or other properties of the lattice.

The manufacturing method or platform may encompass any process known in the art suitable for the selected material. Exemplary additive manufacturing techniques include, for example, electron beam-direct digital manufacturing, direct metal laser sintering, laser-engineered net shapes, ion fusion formation, selective laser sintering, electron beam melting, inkjet printing by selective deposition of binder onto a powder layer, laminated object manufacturing, steroelithography, and continuous liquid interface productions.

Medical Implants of the Invention. In one aspect, the scope of the invention encompasses novel medical implants comprising TBI lattices. The novel implants of the invention encompass devices that can be used in spinal fusion or other types of bone fusion procedures. Implants used as spacers with the intent of bony bridging through the implant will be referred to as "interbody implants" even when referring to areas outside the spine. Examples include spacers for high-tibial osteotomy or the bone-metal interface of an acetabular reconstruction implant.

Implants will be described herein as comprising a body, the body defining the size and shape of the implant. The body will conform to the shape and size of the contemplated fusion. In one embodiment, the implant is an anterior lumbar fusion interbody implant. In such implementation, the body may comprise a shape as used in conventional interbody implant or "interbody cage" devices. For example, the body may comprise a wedge shaped object, for example being (when viewed from the superior or inferior position) a trapezoidal, rounded rectangle or square, oval, or circular body. Exemplary interbody fusion implants of the invention are depicted in FIGS. 1A, 1B, 5A, 5B, 5C, and 5D.

The implant may comprise any other body shape. In one implementation the body is of a shape as utilized for other spinal fusions, including implants for transforaminal lumbar interbody fusion, posterior lumbar interbody fusion, and lateral or oblique lumbar Interbody fusion.

In other implementations, the implant may comprise an implant for any other bone fusion procedure. For example, the body may comprise a sacroiliac implant, an implant for high tibial osteotomy, or a strut allograft to repair a bony defect in a long bone.

The body of the implant will comprise one or more "graft windows." A graft window, as used herein, is a channel or other portion of the implant that is designed to accommodate bone graft material and through which continuous bone is intended to grow. In the implants of the invention, the graft window comprises a novel architecture comprising a trabecular bone structural mimic. Trabecular, or cancellous bone, as found in native bone tissue, is a porous bone comprising a lattice of bony processes, called trabeculae. The trabeculae consist of a complex heterogeneous distribution of interconnecting rod-like and plate-like structures. These rods and plates are largely aligned to provide mechanical strength along the primary axis of stress in the bone while also providing sufficient biomechanical strength against other vectors of stress as well as porosity or open channels allowing the transit of cells, fluids, and other materials through the structure and within the structure.

The inventors of the present disclosure have advantageously determined that a trabecular bone replica, i.e., structural mimic, creates an optimized environment for bone tissue growth from seeded bone graft material. The trabecular bone structure advantageously provides unknown physical factors that promote vigorous and ordered bone tissue development from bone graft material, while providing superior strength and structural support during bone formation. The trabecular bone replica, if derived from a bone having a predominant axis of mechanical strength, will have a predominant axis of mechanical strength and may be deployed a body site wherein it will be subjected to a predominant axis of mechanical stress. For example, It may be deployed as a lumbar or other spinal implant such that the predominant axis of mechanical strength is aligned in an inferior to superior alignment.

In one embodiment, the trabecular bone mimic comprises a plurality of irregularly intertwined plates, forming a porous matrix. The plates may be twisted, for example in a helical manner and/or may have a ribbed or irregular surface to increase surface area. The plates will be anisotropically arranged in alignment with the axis of compressive stress experienced by the implant. For example, in the case of spinal interbody implants, the predominant axis of the ribbons will be along a superior to inferior axis, in alignment with the vertical forces applied to the interbody by the vertebrae surrounding it. The ribbons may be cross-linked by struts or protrusions from adjoining ribbons.

The relationship between plates and rods is essential in contributing to the anisotropic mechanical strength of trabecular bone. During osteoporosis and other metabolic bone disease, there is a conversion from plate-like to rod-like trabecular structures. That is, the density of relative bone in total volume can predict elastic modulus and yield strength of bone on-axis, but does not predict anisotropic mechanical properties appropriately. Computational models that consider rod and plate geometry do accurately predict anisotropic mechanical strength.

While plates are mechanically superior to rods, the spatial combination of rods and plates, as well as their orientation in space, optimizes mechanical strength while minimizing mass and volume and allowing sufficient interconnectivity. Optimization of stiffness can also be controlled with the spatial combination of plates and rods; depending upon the location within the body, a different implant stiffness may be desired. Measurements such as total trabecular volume relative to the measured volume, trabecular number within a specified volume, trabecular thickness within a specified volume, and trabecular separation within a specified volume can be used to describe the geometry. Other parameters such as connectivity density, measuring the degree of interconnectivity of individual trabecular and degree of anisotropy, which assess the degree to which trabeculae are oriented along an axial direction within a volume can be used.

The total volume of trabecular-like material relative to overall volume of the graft window may have a range of 5 to 40% depending on the desired strength or porosity of the implant.

Measurements of trabecular number, trabecular thickness, trabecular separation, and connectivity density will differ depending on the material used. In the case of human bone, typical values are a trabecular number per unit length of 0.1/mm-3.0/mm, trabecular thickness of 0.05 to 0.35 mm, trabecular separation 0.3-2.5 mm, and connectivity density of $0.5/mm^3$ to $5.0/mm^3$.

Figure 1A:
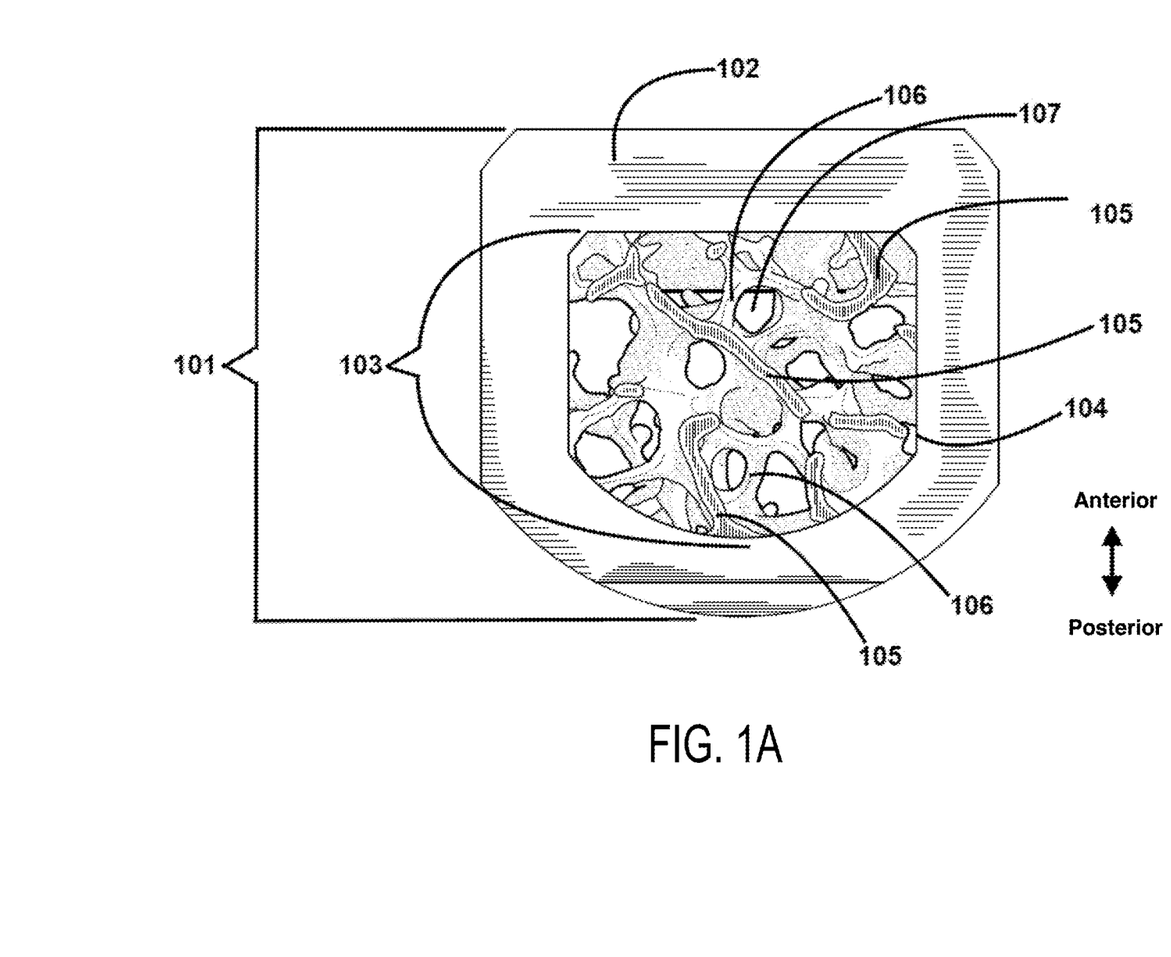
FIG. 1A depicts a top view of an exemplary spinal interbody implant of the invention 101, comprising an outer ring of material 102 and in inner graft window containing a trabecular inspired lattice. The lattice comprises a plurality of substantially vertically aligned plates 105 and substantially horizontally aligned rods 106, the plates and rods being connected to the inner wall 104 of the graft window. The lattice comprises a plurality of airspaces and channels 107.
Figure 1B:
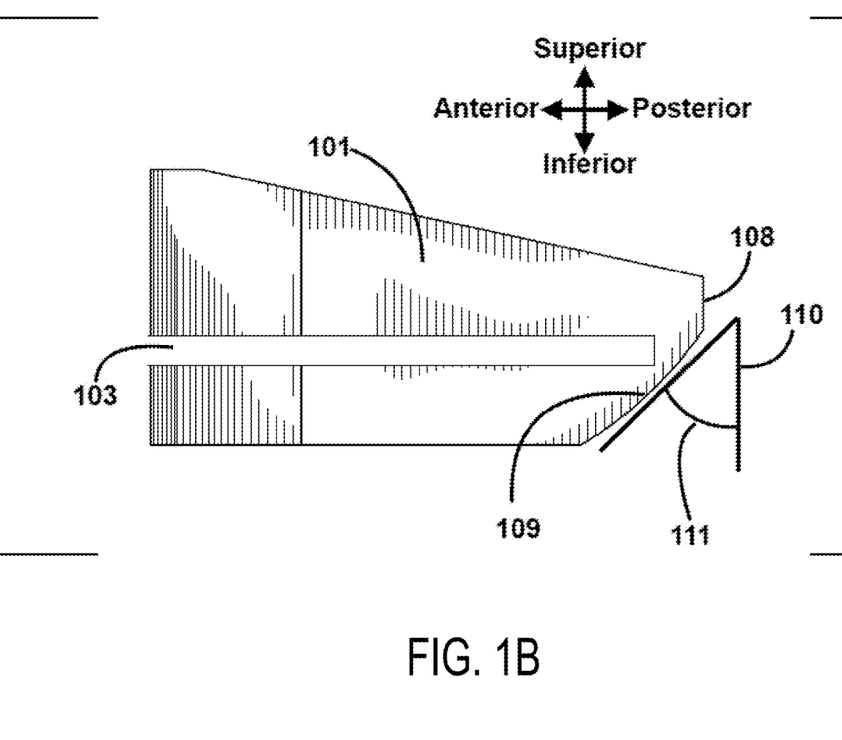
FIG. 1B is a side view of the implant, showing the optional groove 103 and sloped posterior surface 109, which may be described by an angle 111 defined by the deviation of the sloped posterior face from vertical.
Figure 2A:
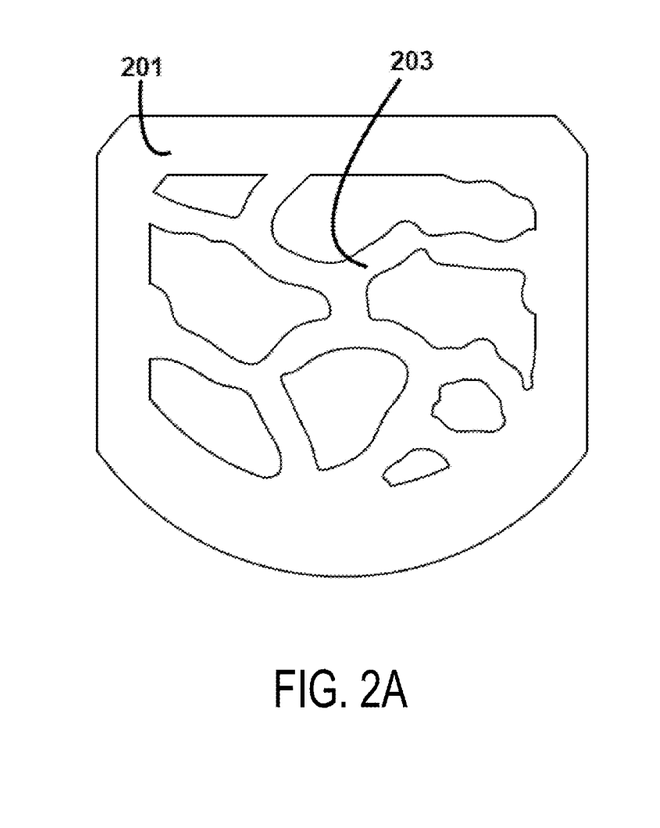
FIGS. 2A and 2B depict cross sections of the plates of two spinal interbody implants, one 201 having thicker plates 203 and one 202 having thinner plates 204.
Figure 2B:
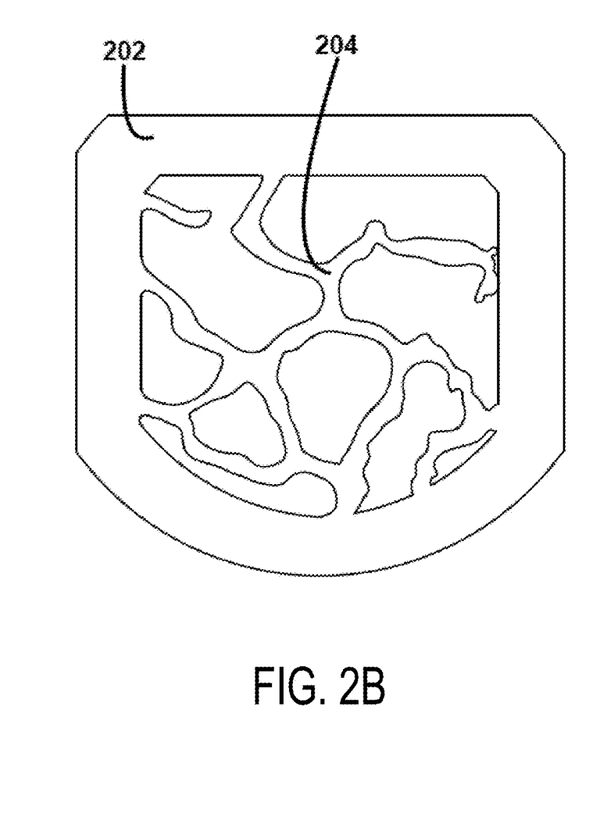
Figure 3A:
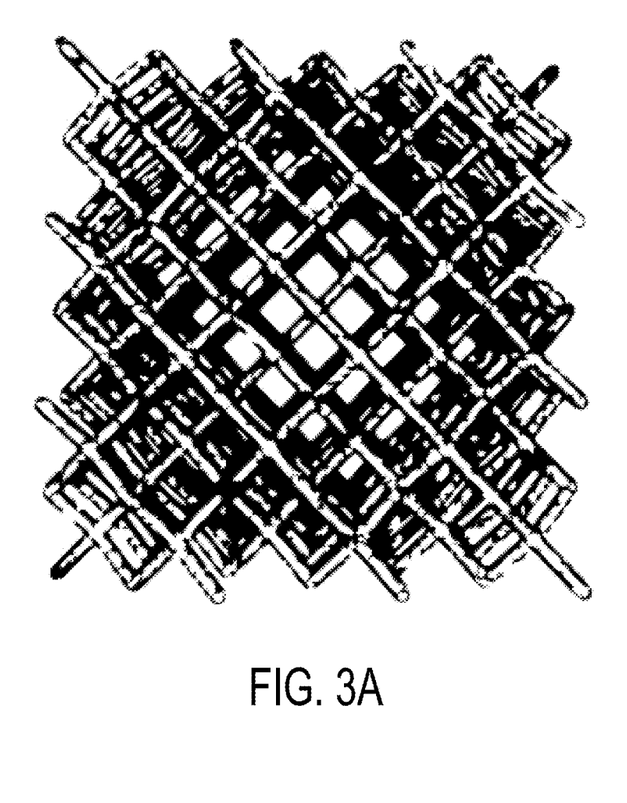
FIG. 3A depicts a side view of an isometric mesh and FIG. 3B depicts a top view of he mesh, wherein, the pore space is equivalent when viewed from the top or the side.
Figure 3B:
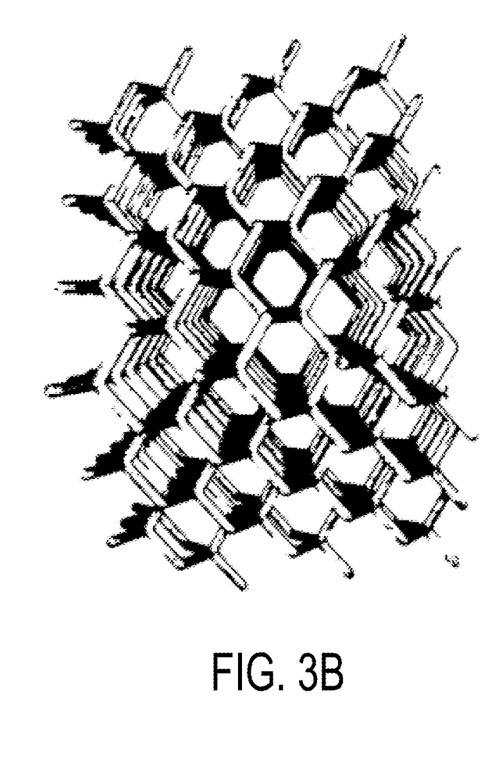
Figure 3C:
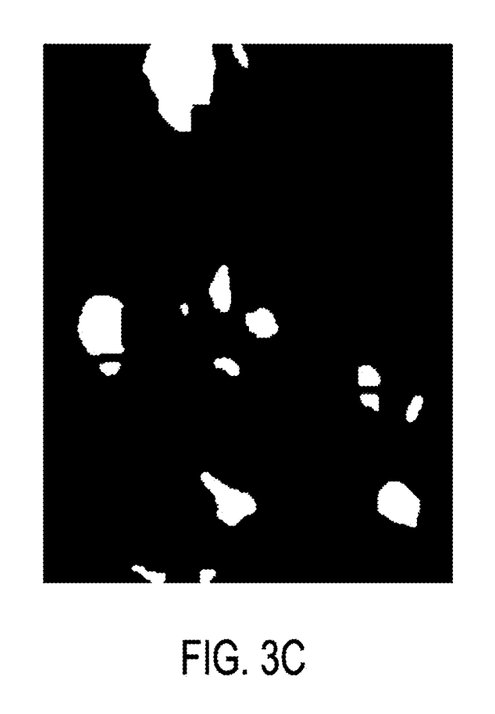
FIGS. 3C and 3D depict a silhouette side view (3C) and a silhouette top view (3D) of a trabecular bone replica lattice, wherein the bone is highly anisotropic, with a top to bottom predominant axis of mechanical strength. Continuous pore space (white) is much more prevalent from the top than the side, reflecting the highly anisotropic nature of the bone replica lattice.
Figure 3D:
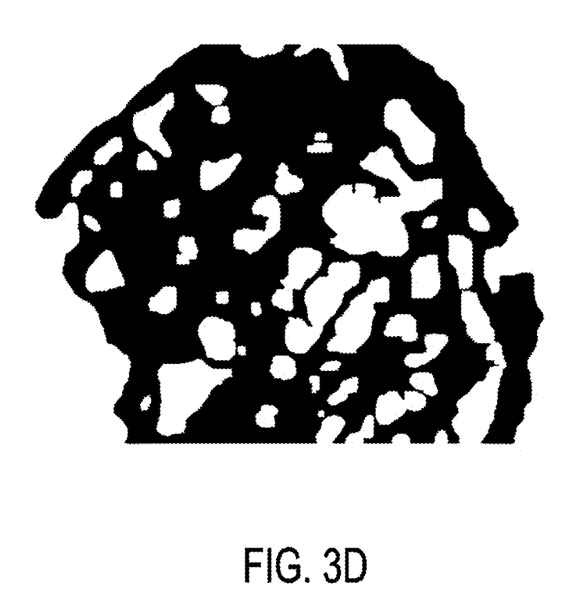
Figure 4A:
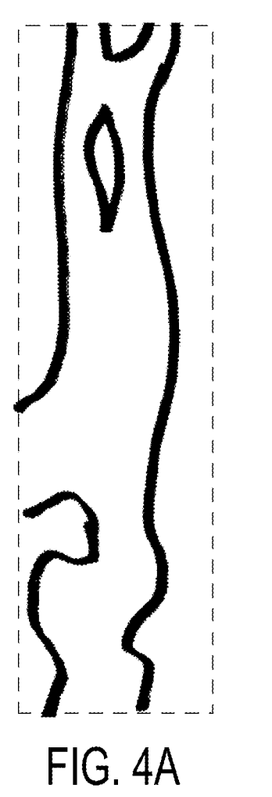
FIGS. 4A, 4B, and 4C depict irregular plate structures inspired by trabecular bone.
Figure 4B:
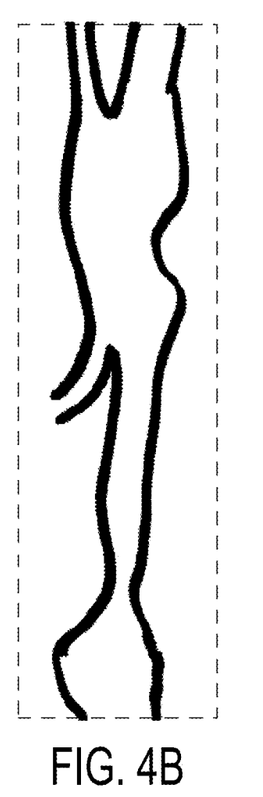
Figure 4C:
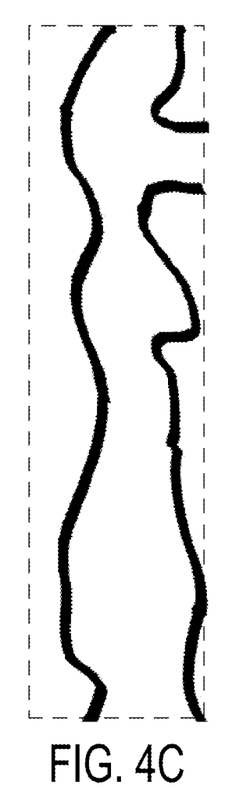

An exemplary posterior lumbar interbody fusion implant of the invention is depicted in FIGS. 1A and 1B. The body comprises a rounded trapezoidal or "bread slice" shape. The body comprises an outer ring of solid material (102) enclosing an inner graft window portion filled by the trabecular inspired lattice structure (103). The implant also comprises an anterior to posterior slot or groove (103), as described below. There is additionally a posterior (111) slope or recess on the inferior surface that will accommodate the natural curvature of the posterior superior portion of inferior lumbar bone.

The TBI can be oriented along the superior to inferior axis of the vertebral body. In other embodiments of the invention, the trabecular mimic structure is oriented in a manner to provide the optimal mechanical strength against the load or torque generated by surrounding structures at the location of the implant, relative to the spine in the patient (for example, a reverse-leaning implant may benefit from a forward-leaning orientation of the TBI structure).

In one embodiment, the implant comprises a "window" being a single hollow channel spanning an axis of the interbody device. For example, if visibility across the graft window is desired, for radiographic assessment of bone-through-growth or fusion, a lateral channel may be included that spans the outer body and inner lattice of the implant, for example, as in the rectangular channel depicted in FIGS. 5A, 5B, 5C, and 5D. Such visibility may be beneficial when the interbody device is manufactured with a radioopaque material such as Ti6Al4V-ELI. Such a secondary lattice or hollowed window may not be necessary if the interbody device has been manufactured with a material such as PEEK, PEKK or other radiolucent material Recessed Posterior Lumbar Interbody Fusion Implant. In one aspect, the scope of the invention encompasses an improved anterior lumbar interbody fusion implant, the improvement comprising a posterior recessed slope. This posterior slope enables the implant to fit to the irregular target site in the lumbar spine. The posterior slope comprises a recession that allows the upward slope of the superior portion of the inferior vertebral body to fit in without angling the implant itself. A posterior recess is depicted in FIG. 1B, with recessed slope circled in red and the yellow line indicating pure vertical. The posterior recess is a sloping edge of any angle, for example, from 10-80 degrees, for example, an angle of about 20-40 degrees, for example, about 10, about 15, about 20, about 25, about 30, about 35, about 40, about 45, about 50, about 55, about 60, about 65, about 70, about 75 or about 80 degrees, with about being within 2-3 degrees of the enumerated value. For example, the posterior slope may begin in the posterior portion of the interbody device, at least 25% from the posterior edge and at least a 30 degree slope and less than a 90 degree (pure vertical) slope relative to the inferior surface. The slope generally spans the entire width of the implant from medial to lateral, but can be less than the entire width, for example if the implant is larger than the inferior vertebral body.

Grooved Interbody Fusion Implant. In another aspect, the scope of the invention encompasses an improved interbody fusion implant with modified flexibility. This flexibility enables surgeons to properly place the implant with greater ease, reducing surgery time and trauma to the treated area. Mismatch between the inferior surface, even with the presence of recessed portion can occur. The groove may comprise a planar groove or channel that bisects the implant to allow mild deformation of the implant. The size of the groove is dependent on the material used for the implant but the amount of potential deformation must be below the failure strain of the device. For example, in the groove may be of a width of 1-3 mm.

The slot/groove (103) can be a hollow portion of the implant to allow for some flexibility, with one or more bridging regions of material connecting the sections of the body on either side of the groove. In one embodiment, the groove region comprises a solid component made from a different material than the implant body, wherein the second material filling the groove has lower stiffness. In another embodiment, the material within the groove may be bioabsorbable or biodegradable. The slot and groove can be placed in different geometries to bias the direction of flexibility in the coronal, sagittal, or axial planes, as well as multiplanar directions.

In one implementation, the groove is parallel to the surfaces of the layer alignment of a 3D printed model, with the groove extending from the anterior side to 70 to 80% of the anterior to posterior axis of the body. In one embodiment the groove extends along the entire perimeter of the body, with one or more bridging regions that connect the upper and lower halves. In one implementation, the groove is partially filled in selected regions with a second material having different material properties than the main implant body. In other embodiments, more than one groove exists, for example, in coronal, sagittal, axial planes, or in a multiplanar direction.

Typically, a single groove is used. However, with will be understood that two or more grooves may be employed to impart variable flexibility to the implant.

An exemplary posterior lumbar interbody fusion implant with the groove of the invention (103) is depicted in FIG. 1B.

The groove and posterior recess improvements may be employed in lumbar interbody fusion implants of any type, including both prior art implants and the novel trabecular bone mimic implants of the invention.

Furthermore, the groove and posterior recess concept can be utilized in any other spinal interbody or other fusion implant. The scope of the invention encompasses any such implant comprising one or more longitudinal grooves that impart flexibility to the implant or posterior recess in a spinal implant.

Methods of Use. The scope of the invention further extends to methods of using the novel implants in fusion procedures. In one aspect, the invention encompasses a method of fusing two bony structures by placement of an implant between and in contact with the two bony structures, wherein the implant comprises one or more graft windows comprising a trabecular bone structural mimic. In one embodiment, the fusion procedure is a posterior lumbar interbody fusion procedure and the implant is a posterior lumbar interbody fusion implant. In one embodiment, the implant comprises 3D printed PEEK. In another embodiment, the implant comprised 3D printed Titanium or Titanium alloy.

The implants of the invention are utilized in combination with bone graft material, which is packed into the hollow spaces of the trabecular bone structural mimic. Typical bone graft materials include autologous bone tissue, bone marrow aspirate, demineralized bone matrix, demineralized bone matrix with handling or carrier agents, bioactive ceramics, porous scaffold material infused with bone morphogenic protein and/or cells. In some embodiments of the invention, no added bone graft will be used.

Industrial Applications of Trabecular Lattice. The TBI lattices of the invention may deployed in various articles of manufacture. In various implementations, the TBI lattice is incorporated into an article of manufacture, for example encased within an outer shell or other body. In one embodiment, the TBI lattice surrounds or is mounted to one or more support bodies. In one embodiment, the substantially the entire article of manufacture consists of TBI lattice.

In certain implementations, the TBI lattice is an anisotropic lattice wherein the object has increased mechanical strength in one or more axes.

In certain implementations, the TBI lattice comprises one or more regions of increase structural strength.

In one implementation, the objects comprising TBI lattice include protective safety gear such as helmets, pads, body armor, and shields.

In one implementation, the objects comprising TBI lattice are parts for vehicles such as automobiles, bicycles, boats, and aircrafts. The TBI lattice may be incorporated into various parts, including, for example, vehicle, boat or aircraft outer body panels, ribs, struts, frames, and military vehicle armor.

In one implementation, the object comprising TBI lattice is an automobile bumper. For example, in a frontal automotive bumper, anisotropic resistance is valuable. Pure single-axis resistance from a direct frontal impact would only be beneficial if the impact was directly from the front. An oblique impact or offset impact would require a lattice that had multi-directional resistance to come from the passenger or driver side. Last, while there is limited vertical strength required given the improbable scenario of a front car bumper providing resistance against a pure sky-to-ground direction, or ground-to-sky direction, some vertical strength is needed to account for mismatch in bumper heights, such as an SUV or truck striking a passenger car and low sports car. A front bumper design with an anisotropic TBI lattice can provide this multidirectional strength, yet prioritized against frontal impacts.

In certain implementations, a subset of the TBI lattice components comprises hollow bodies through which gas or liquid may be flowed, for example, in the context of heat exchange. For example, the plates or rods or a subset of plates and/or rods may be hollow. For example, a typical car radiator has cooling fins that utilizing in coming air to cool down circulating coolant. With these traditional fin designs, the transit time of the air is very short as the air enters and exits in the same plane. Using TBI lattices, that are based on the plate and rod structure, incoming air can be redirected, increasing transit time across the heat exchanger, without increasing flow resistance. In one embodiment, the object comprising TBI lattice is a radiator, such as an automobile radiator, comprising hollow elements through which coolant is circulated. In one embodiment, the automobile radiator comprises an anisotropic TBI lattice wherein the predominant axis of mechanical strength is aligned with the front to back axis of the automobile in order to impart structural as well as cooling functions to the radiator.

Similarly, the flow of liquid coolant can also be directed in a similar manner through a complementary, organized lattice structure made of a thermally conductive material such as aluminum or copper to improve cooling. This would be achieved by placing a TBI lattice inside a pipe and cooling the pipe containing the lattice. Additionally, a counter-current temperature/flow gradient can be achieved with optimization of these internal lattices.

EXAMPLES

Example 1. 3-D Printed Prototype

A section of trabecular bone from the T12 vertebra was scanned by three-dimensional CT high resolution imaging. The scan data was used in designing an anterior lumbar interbody fusion implant. The implant design comprised an outer ring of solid material surrounding a graft window comprising a scaled replica of the scanned bone. The implant design further included a posterior recess and anterior groove. The design was employed in a high temperature PLA 3D printing system, creating the PLA implant depicted in FIGS. 1A and 1B.

Different parameters for the trabecular density and trabecular widths can be used to achieve different goals. An increase in density and/or trabecular width can increase the short-term biomechanical strength of the device. A decrease in density and/or trabecular width typically will increase later bony growth and bony structure. The selection of the parameters can be patient specific and will also be material specific. Titanium is an alternative material that can be used with increased strength, thereby allowing less trabecular thickness and/or trabecular density.

Example 2. 3-D Printed Prototype

Figure 5A:
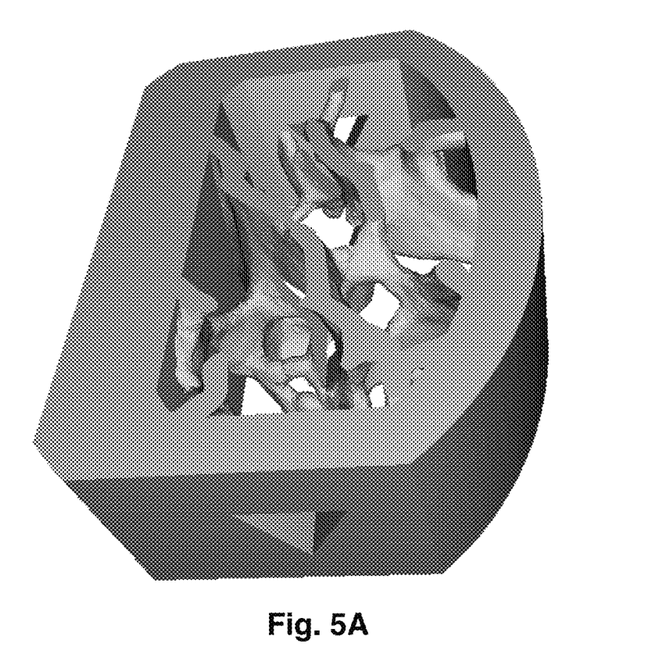
FIGS. 5A, 5B, 5C, and 5D depict different views of a titanium 3D printed interbody implant having a central trabecular bone inspired lattice. The implant includes a triangular window and central channel that enables unimpeded radiographic imaging from a lateral perspective such that bone material within the implant may be imaged and monitored.
Figure 5B:
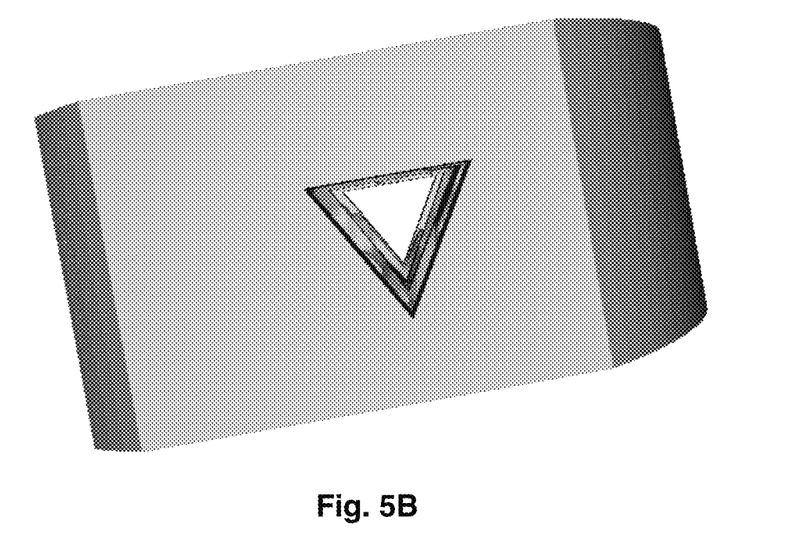
Figure 5C:
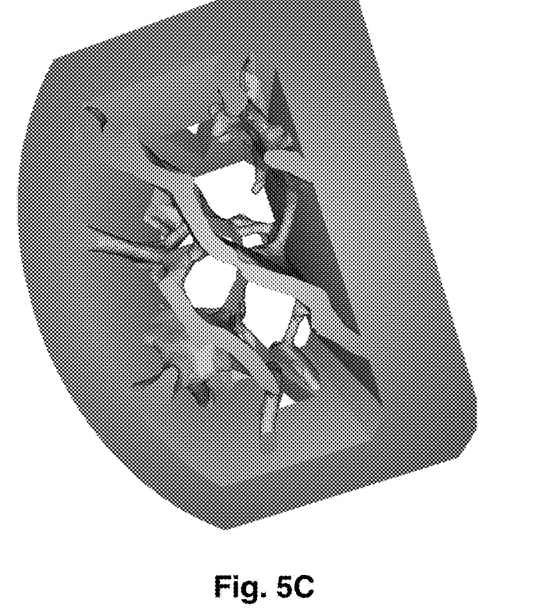
Figure 5D:
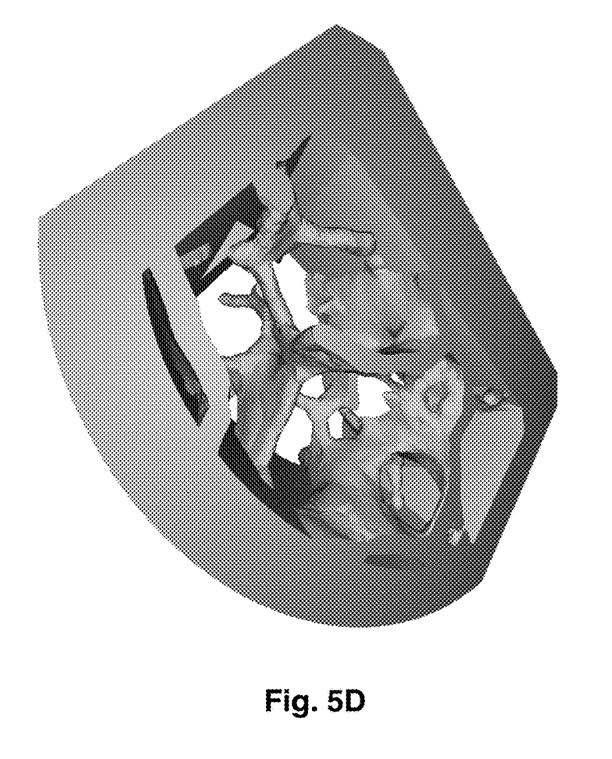

Titanium 3D printed implant. An implant, substantially as depicted in FIG. 5A, was printed using They are printed using a laser sintering technique with a 500 W fiber laser, in grade 23 Titanium Alloy.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. An article of manufacture comprising a trabecular bone-inspired lattice, the trabecular bone-inspired lattice comprising
    a plurality of plates, wherein each plate comprises a ribbon structure comprising a length, width and thickness and having a predominant axis, wherein over 40% of the plates are anisotropically arranged such that the predominant axis of each plate is in alignment with a predominant axis of mechanical strength of the trabecular bone-inspired lattice; and
    a plurality of rods, wherein each rod comprises an elongated structure and wherein the plurality of rods interconnects the plates with one another.

2. The trabecular bone-inspired lattice of claim 1, wherein
    the width of each plate is between 2 and 50 times its thickness; and
    the length of each plate is between 2 and 100 times the width of the plate.

3. The trabecular bone-inspired lattice of claim 1, wherein each plate comprises an elongated rectangle.

4. The trabecular bone-inspired lattice of claim 1, wherein each plate comprises an elongated, irregular structure.

5. The trabecular bone-inspired lattice of claim 1, wherein the plates comprise a ribbed, concave, or convex surface.

6. The trabecular bone-inspired lattice of claim 1, wherein each plate is twisted or helical.

7. The trabecular bone-inspired lattice of claim 1, wherein the rods are flat, square, circular, or irregular.

8. The trabecular bone-inspired lattice of claim 1, wherein 40% to 90% of the plates align anisotropically along the predominant axis of mechanical strength of the lattice.

9. The trabecular bone-inspired lattice of claim 1, wherein different subsets of the plates align along two or more predominant axes of the lattice.

10. The trabecular bone-inspired lattice of claim 1, wherein the trabecular bone-inspired lattice is surrounded by a cage comprising a shell or lattice.

11. The trabecular bone-inspired lattice of claim 1, wherein the lattice comprises one or more localized volumes of an increased measure of mechanical strength, relative to an average mechanical strength measured over a volume of the trabecular bone-inspired lattice.

12. The trabecular bone-inspired lattice of claim 11, wherein the one or more localized volumes of an increased measure of mechanical strength comprises one or more features selected from an increased width and/or thickness of plates, increased density of rods, increased width, thickness, and/or diameter of rods, and increased alignment of plates.

13. The trabecular bone-inspired lattice of claim 1, wherein the lattice has a structural model index between 0.5 and 3.5.

14. The trabecular bone-inspired lattice of claim 1, wherein the lattice has an ellipsoid factor is between −0.5 and 0.5.

15. The trabecular bone-inspired lattice of claim 1, wherein the lattice has a degree of anisotropy between 0.5 and 3.0.

16. The trabecular bone-inspired lattice of claim 1, wherein the lattice comprises a replica of a trabecular bone structure.

17. The trabecular bone-inspired lattice of claim 16, wherein a source bone on which the replica is based comprises bone having a predominant axis of mechanical stress.

18. The trabecular bone-inspired lattice of claim 1, wherein the lattice is made by additive manufacturing.

19. The trabecular bone-inspired lattice of claim 1, wherein the lattice comprises a material selected from stainless steel, titanium, aluminum, copper, cobalt chrome, PEEK, ultrahigh molecular weight polyethelene, polyphenylsulfones, polyetheramide materials, polylactic acid, nylons, polymeric material coated with metal, and woven carbon fiber reinforced plastics.

20. The trabecular bone-inspired lattice of claim 1, further comprising a groove or channel.

21. The trabecular bone-inspired lattice of claim 1, further comprising a window to allow imaging of bone graft material.

22. The trabecular bone-inspired lattice of claim 1, further comprising bone graft material, wherein the bone graft material is contained in hollow spaces within the trabecular bone-inspired lattice.

23. The trabecular bone-inspired lattice of claim 22, wherein the bone graft material comprises autologous bone tissue, bone marrow aspirate, or demineralized bone matrix.

24. The trabecular bone-inspired lattice of claim 22, wherein the bone graft material further comprises bone morphogenic protein.

* * * * *

UNITED STATES PATENT AND TRADEMARK OFFICE
CERTIFICATE OF CORRECTION

| | | |
|---|---|---|
| PATENT NO. | : 11,717,418 B2 | Page 1 of 2 |
| APPLICATION NO. | : 17/040453 | |
| DATED | : August 8, 2023 | |
| INVENTOR(S) | : Alan Dang et al. | |

It is certified that error appears in the above-identified patent and that said Letters Patent is hereby corrected as shown below:

On the Title Page

In item (57), in Column 2, in "Abstract", Line 14, delete "the the" and insert -- the --.

In the Specification

In Column 1, Line 54, delete "thoracumbular" and insert -- thoracolumbar --.

In Column 1, Line 59, delete "the the" and insert -- the --.

In Column 1, Line 61, delete "(Medtroinc" and insert -- (Medtronic --.

In Column 3, Line 42, delete "he" and insert -- the --.

In Column 5, Line 36, delete "Fore" and insert -- For --.

In Column 6, Line 65, delete "lattice" and insert -- lattice. --.

In Column 7, Line 61, delete "radioopaque" and insert -- radiopaque --.

In Column 9, Line 23, delete "forces" and insert -- forces. --.

In Column 9, Line 34, delete "additive" and insert -- Additive --.

In Column 9, Line 43, delete "substrate" and insert -- substrate. --.

In Column 9, Line 49, delete "polyethelene," and insert -- polyethylene, --.

In Column 9, Line 50, delete "polyetheramide" and insert -- polyetherimide --.

Signed and Sealed this
Sixth Day of August, 2024

Katherine Kelly Vidal
*Director of the United States Patent and Trademark Office*

In Column 10, Line 3, delete "steroelithography," and insert -- stereolithography, --.

In Column 12, Line 14, delete "radioopaque" and insert -- radiopaque --.

In Column 12, Line 18, delete "material" and insert -- material. --.

In the Claims

In Column 16, Line 38, in Claim 19, delete "polyethelene," and insert -- polyethylene, --.

In Column 16, Line 39, in Claim 19, delete "polyetheramide" and insert -- polyetherimide --.